United States Patent [19]

Clegg et al.

[11] Patent Number: 5,074,846
[45] Date of Patent: Dec. 24, 1991

[54] STOMA CREATOR GASTROSTOMY DEVICE AND METHOD FOR PLACEMENT OF A FEEDING TUBE

[75] Inventors: Robert D. Clegg, Pickerington, Ohio; Ronald M. Isaac, Libertyville, Ill.; William H. Hirsch, Columbus, Ohio

[73] Assignee: Abbott Laboratories, Abbott Park, Ill.

[21] Appl. No.: 581,952

[22] Filed: Sep. 13, 1990

[51] Int. Cl.⁵ .............................................. A61M 5/00
[52] U.S. Cl. .................................. 604/164; 604/158; 604/53; 604/191; 604/283; 606/191; 285/334.2; 285/334.5
[58] Field of Search .................. 606/191, 194; 604/53, 604/158, 154, 270, 271, 272, 280, 281, 282, 283; 138/155; 285/334.2, 334.3, 334.5, 398

[56] References Cited

U.S. PATENT DOCUMENTS

| | | | |
|---|---|---|---|
| 596,787 | 1/1898 | Perkins | 285/334.3 |
| 2,751,911 | 6/1956 | Held | 604/283 |
| 3,918,450 | 11/1975 | Patel | 604/280 |
| 3,982,544 | 9/1976 | Dyck | 604/280 |
| 4,231,596 | 11/1980 | Ridenour | 285/398 |
| 4,668,217 | 5/1987 | Isono | 604/280 |
| 4,878,900 | 11/1989 | Sundt | 604/283 |
| 4,969,879 | 11/1990 | Lichte | 604/283 |

FOREIGN PATENT DOCUMENTS 1193759  6/1968  United Kingdom ................ 604/283

Primary Examiner—Francis Jaworski
Assistant Examiner—Scott R. Akers
Attorney, Agent, or Firm—Lonnie R. Drayer; Donald O. Nickey

[57] ABSTRACT

A stoma creator is provided comprising a flexible tube having a first opening, a tapered dilator portion, having a second opening, the diameter of the first opening being greater than the diameter of the second opening, and a connecting portion. The stoma creator has a tapered dilator having a side wall which gently tapers from approximately 5 French to 14 French. The method for using the device of this invention comprises the step of securing the stomach to the abdominal wall through the use of T-fasteners, inserting a needle percutaneously into the gastric lumen, passing a guidewire through the needle, grasping the guidewire with the endoscope and bringing it out through the mouth, threading the tapered dilator over the guidewire and passing the stoma creator down the throat into the stomach then out through the abdominal wall the stoma creator cutting of the tapered dilator and connecting portion, passing a gastrostomy tube through the flexible tube, with the gastrostomy tube having a balloon adjacent its tip, removing the flexible tube while leaving the guidewire in place, filling the balloon, and withdrawing the guidewire. A similar alternative method is also disclosed.

3 Claims, 5 Drawing Sheets

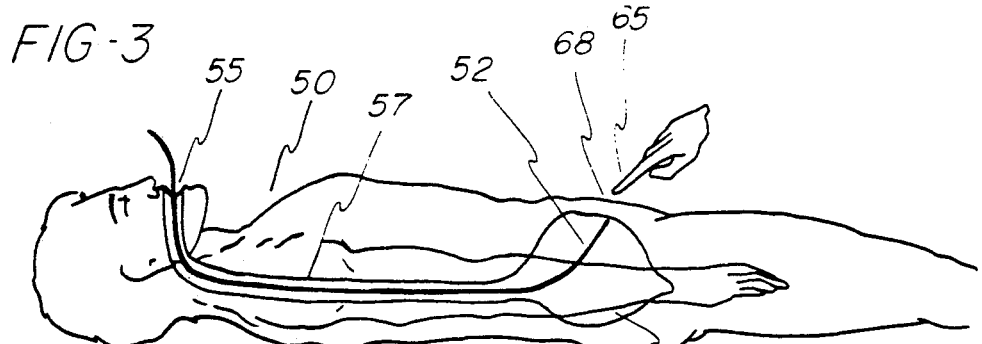
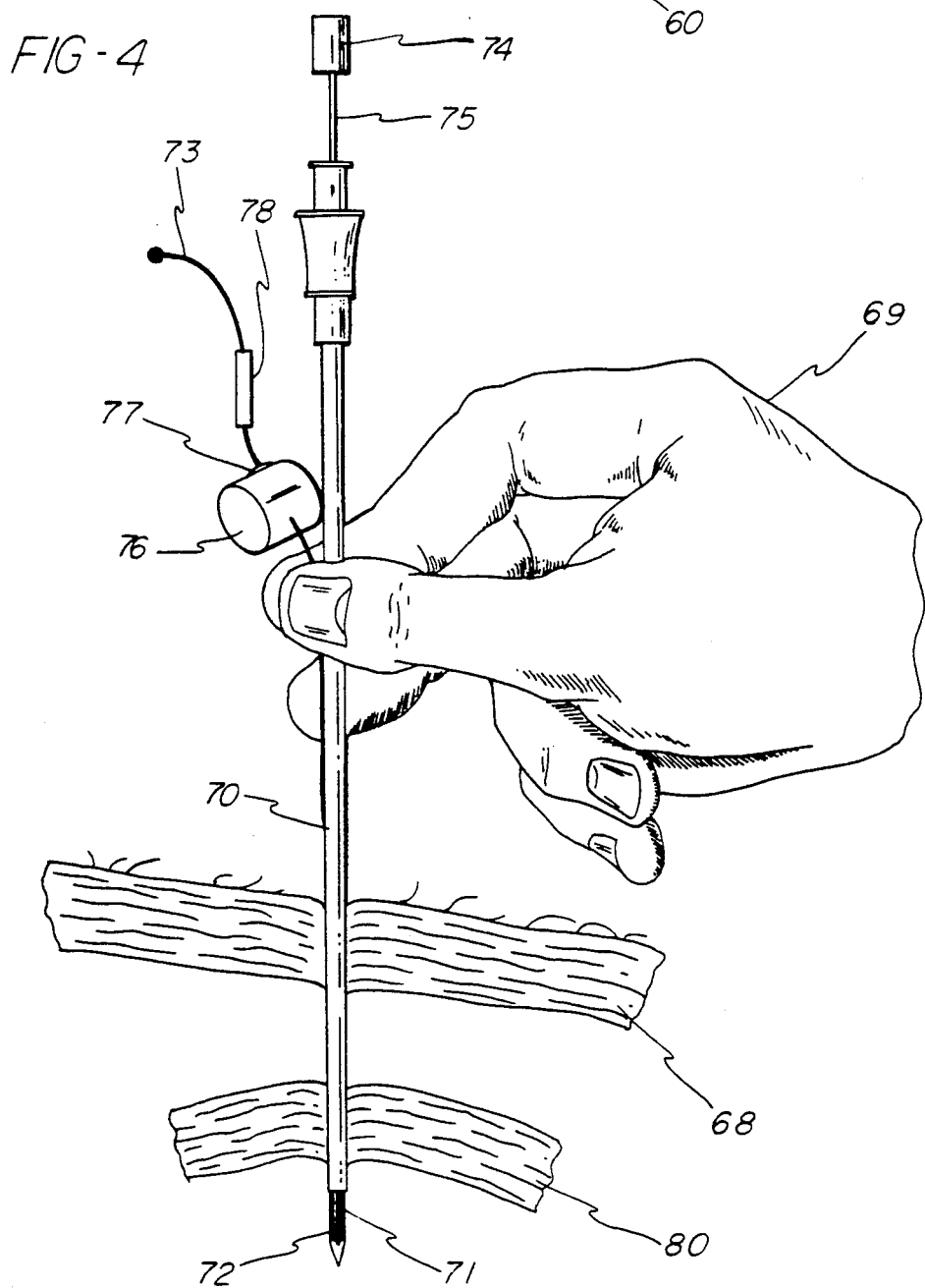

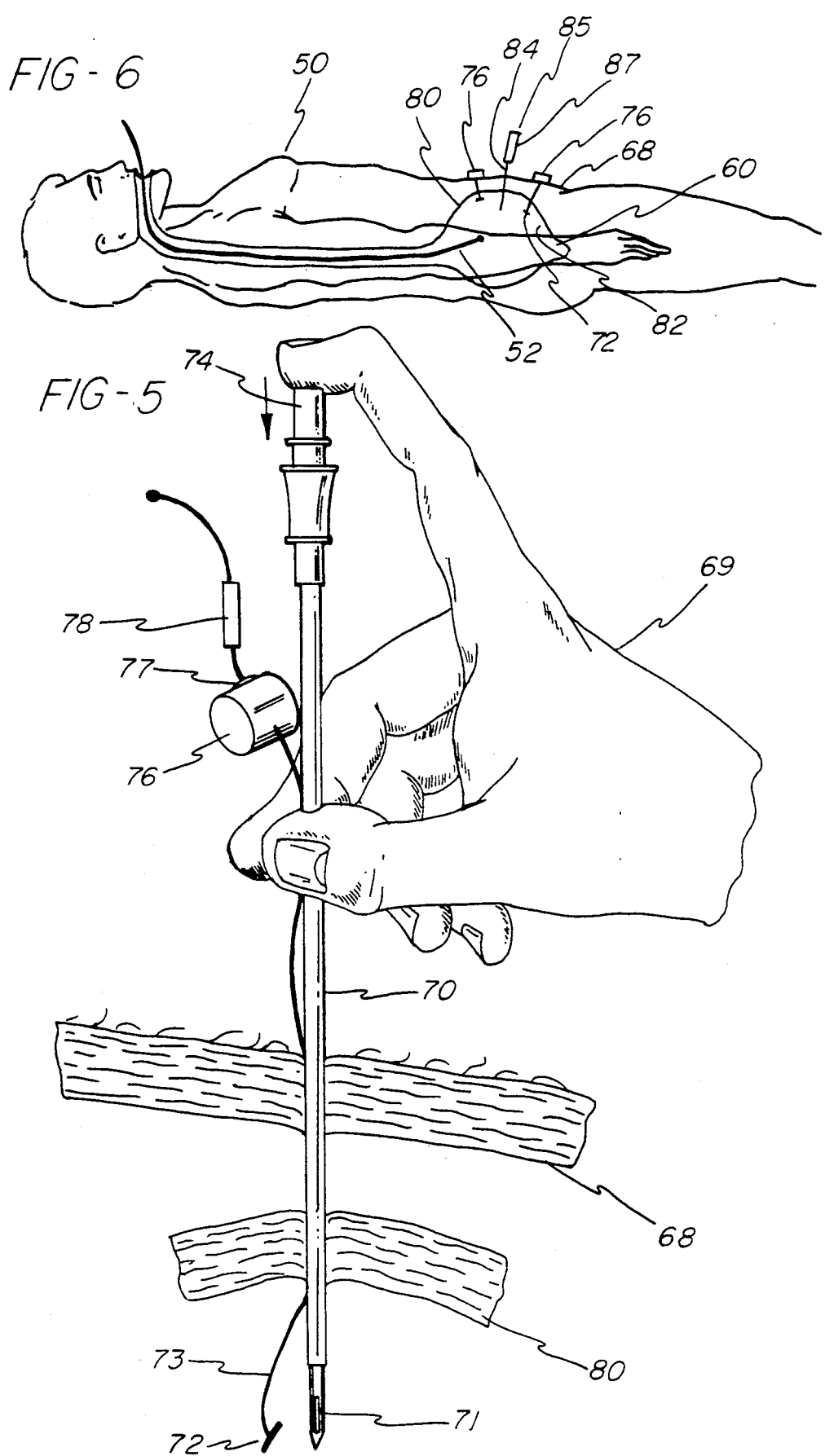

STOMA CREATOR GASTROSTOMY DEVICE AND METHOD FOR PLACEMENT OF A FEEDING TUBE

The present invention relates generally to a gastrostomy device that can be used in the placement of a feeding tube, and more particularly, to a stoma creator and a method for using it in the endoscopic or fluoroscopic placement of a catheter into a patient for subsequent use in supplying enteral nutrition, medications, and other fluids into the stomach or small bowel.

BACKGROUND ART

Many individuals in health care facilities or those cared for at home are able to achieve sufficient caloric intake through eating standard diets and prepared meals. However, a sizable number of such patients are unable to ingest enough solid food to meet their body's nutritional needs. Examples of these individuals would include stroke or neurologically impaired patients, who have lost their ability to swallow effectively; critically ill, weak or comatose patients, who may be unable to chew sufficient quantities of food; patients suffering from obstructive lesions, such as cancer of the esophagus, who may be unable to swallow their food; and patients with head and neck trauma, such as fractured jaws and gunshot wounds who cannot chew solid food. For these patients, although caloric supplementation through parenteral, also known as intravenous feeding, is an option, enteral nutrition support is the more preferable method.

In response to this problem, liquid foods (medical nutritionals) have been developed for enteral feeding. The technique of enteral nutrition support initially utilizes a nasogastric tube to transport the liquid nutritional products from a container through the patient's oropharynx and thence into the stomach. However, there are well described complications associated with long term use of a nasogastric tube, and if after four to six weeks of use the inability to effectively swallow remains, patients should be switched to a gastrocutaneous feeding port. The gastrostomic feeding device or gastric portal, is placed into a gastrocutaneous stoma with the device typically featuring a relatively cylindrical component which extends through the stoma, and a tip portion which precludes easy withdrawal of the port from the stoma.

While it is possible to place the gastric port by means of a surgical procedure utilizing a general or local anesthetic, the preferred method for placement of these ports is percutaneous endoscopic gastrotomy (PEG) that involves use of an endoscope to visualize the insertion site on the gastric mucosa and the subsequent creation of an artificial opening into the stomach through the abdominal wall under local anesthesia.

Currently medical personnel can use one of three procedures in conjunction with the conducting of a percutaneous endoscopic gastrostomy. One procedure, known as Sacks-Vine, involves passing an endoscope down the throat until its terminus is in the interior of the stomach. A Seldinger needle is then externally inserted through the various tissue layers until it enters the stomach at a predetermined point. The needle is retracted leaving only the Seldinger cannula in place and a guidewire is then inserted through the stoma. The terminal end of the guidewire is grabbed by the endoscope and retracted up the throat. A tapered dilating catheter attached to the gastrostomy port is passed over the guidewire then inserted down the throat, through the esophagus and into the stomach so as to form, upon removal of the catheter through the abdominal skin, an opening wide enough to accommodate the trailing gastric port. At the proximal end of the gastrostomy port is a retention device that keeps the proximal end of the catheter from passing through the gastrocutaneous stoma. A feeding set adapter is then hooked up to the portion of the catheter external of the body that allows the gastrostomy port to be used for the actual feeding of the patient.

A second technique is known as Ponsky, wherein a suture or wire with a fixed loop is fed though a needle placed through the abdominal wall and into the stomach and the pulled up the esophagus and out the mouth. Suture or wire with a fixed loop is fixed to the distal end of a tapered dilating catheter that also has a suture or wire with a fixed loop attached to it. The tapered dilating catheter with an attached gastrostomy port is then is pulled down the throat, down the esophagus and into the stomach. Once again, the attached gastrostomy port used in this technique has a retention device at its proximal end. Once the catheter is in place, the adapter is connected and feeding commences in a manner similar to that of Sacks-Vine.

A third technique is known as the Russell technique, wherein a needle is placed through the anterior abdominal wall and into the stomach and a guidewire placed through it. The needle is removed leaving a gastrocutaneous guidewire. A series of dilators, similar to vessel dilators are passed one at a time over the guidewire, thereby enlarging the gastrocutaneous stoma from the outside of the patient. The last dilator may have on it a peel away sheath, which sheath accompanies the terminal end of that particular dilator into the interior of the stomach. Once the sheath is there, the dilator is removed and a balloon catheter is inserted into the peel-away sheath. The sheath is then retracted through the stoma and peeled away from the balloon catheter, which catheter is then filled such that the stomach is held adjacent to the abdominal wall by the interaction of the balloon catheter and a skin disk applied to the outside of the patient's body. A variation of this technique uses a last dilator that is larger than the balloon catheter to be placed, so that when the dilator is removed the gastrocutaneous stoma is large enough to accept the balloon catheter stiffened with a stylet.

Although all three methods permit the performance of a percutaneous endoscopic gastrostomy, the Sacks-Vine and Gauderer-Ponsky techniques, due to the introduction of the feeding tube retention device can cause the patient to experience both trauma and bleeding. Additionally, if there are any esophageal restrictions, the retention devices associated with the tubes utilized in these two techniques cannot pass through the restriction or actually tear or lacerate the tissue around the restriction, coupled with the fact that extra medical attention may be required to retrieve the proximal end of the tube in the case of a problem.

Additionally, the first two techniques typically require another endoscopic procedure for removal of the tube upon cessation of enteral feeding or upon the necessity of changing the tube. This additional procedure results in additional trauma associated with any endoscopic procedure, as well as cost, to the patient. The Russell technique has as its primary disadvantage the fact that if the balloon fails prior to a mature stoma tract being formed, the stomach could fall away from the abdominal wall, leaving an open passage into the peritoneum. This open passage could result in peritonitis.

It is thus apparent that the need exists for an improved stoma creator and a method for using such a device for the primary placement of catheters for the administration of enteral nutrition, medications and other fluids into the stomach or small bowel.

DISCLOSURE OF THE INVENTION

There is disclosed a stoma creator comprising a flexible tube, said flexible tube having a first opening, a tapered dilator portion, said dilator portion having a second opening, the diameter of said first opening being greater than the diameter of said second opening, and a connecting portion. The connecting portion of the stoma creator comprises a first end portion, a first aperture, a tapered section, a second end portion, a second aperture, and a barb. The flexible tube is retained about said first end portion and said dilator is secured to said second end portion. Preferably the tapered dilator is semi-rigid. The flexible tube has a proximal end and a distal end, said first end portion having means for securing said connecting portion to said distal end. The larger size feeding gastrostomy tube is both longer lasting, permits the easier administration of crushed medication, and has less tendency to clog.

There is also disclosed a method for the endoscopic placement of a feeding tube for use in enteral feeding comprising the steps: 1) under endoscopic visualization securing the stomach to the abdominal wall through the use of T-fasteners; 2) inserting a needle percutaneously into the gastric lumen; 3) passing a guidewire through said needle; 4) grasping said guidewire with said endoscope and bringing it out through the mouth; 5) threading the tapered dilator portion of a stoma creator over said guidewire and passing said stoma creator down the throat, into said stomach, and out through said abdominal wall, said stoma creator comprising a flexible tube, a tapered dilator portion, and a connecting portion; 6) cutting off said tapered dilator portion and said connecting portion; 7) passing a gastrostomy tube through said flexible tube, said gastrostomy tube having a balloon adjacent its tip; 8) removing said flexible tube while leaving said guidewire in place; 9) filling said balloon; and 10) withdrawing the guidewire.

This method also can include the step of removing said T-fasteners. The gastrostomy tube utilized in this method is flexible and stiffened with a stylet. The method also includes the external removal of said gastrostomy tube without having to do another endoscopic procedure. The flexible tube and said tapered dilator are adhesively bonded to said connecting portion. The flexible tube is of diameter sufficient to accommodate a 22 French gastrostomy tube. The tapered dilator has a side wall which gently tapers from approximately 5 French to 14 French.

There is also disclosed a method for the endoscopic placement of a feeding tube for use in enteral feeding comprising the steps: 1) under endoscopic visualization securing the stomach to the abdominal wall through the use of T-fasteners; 2) inserting a needle percutaneously into the gastric lumen; 3) passing a guidewire through said needle; 4) grasping said guidewire with said endoscope and bringing it out through the mouth; 5) securing the tapered dilator portion of a stoma creator to said guidewire and passing said stoma creator down the throat into said stomach, then out through said abdominal wall, said stoma creator comprising a flexible tube, a tapered dilator portion, and a connecting portion; 6) cutting off said tapered dilator portion and said connecting portion; 7) passing a gastrostomy tube through said flexible tube, said gastrostomy tube having a balloon adjacent its tip; 8) removing said flexible tube; and 9) filling said balloon.

This method can include the additional step of removing said T-fasteners. The gastrostomy tube used in this method is flexible and stiffened with a stylet. This method can also include the step of external removal of said gastrostomy tube without having to do another endoscopic procedure.

The present invention provides a stoma creator that does not have a cross-bar or similar retention device which must be passed through the esophagus in order to retain the device in the proximal end of the device in the stomach.

A further aspect of the invention is that in order to effect removal of the feeding tube installed by the use of the stoma creator of this invention, a second endoscopic procedure is not required.

Yet another aspect of this invention is that it is less time consuming than some of the other PEG procedures.

Still another aspect of this invention is that it permits the introduction of larger sizes of feeding gastrostomy tubes than can be accommodated in many of the existing procedures.

Still another aspect of the present invention is that it does not require a visit to a physician's office or a hospital emergency or operating room in order to effect change of the feeding tube.

Yet another aspect of the invention is that it provides for a situation wherein, if the feeding tube fails or is inadvertently removed by the patient, the stomach is still affixed to the interior abdominal wall thereby preventing intraperitoneal leakage.

Other aspects and advantages of the invention will be apparent from the following description, the accompanying drawings and the appended claims:

BRIEF DESCRIPTION OF THE DRAWINGS

FIG. 3 is a schematic view showing the method of utilizing the stoma creator of this invention.

FIG. 4 is another schematic view showing the method of practicing the method of this invention.

FIG. 5 is another schematic view showing the practice of the method of the current invention.

FIG. 6 is another schematic view showing the practice of the method of the current invention.

DETAILED DESCRIPTION OF THE INVENTION

Figure 1:
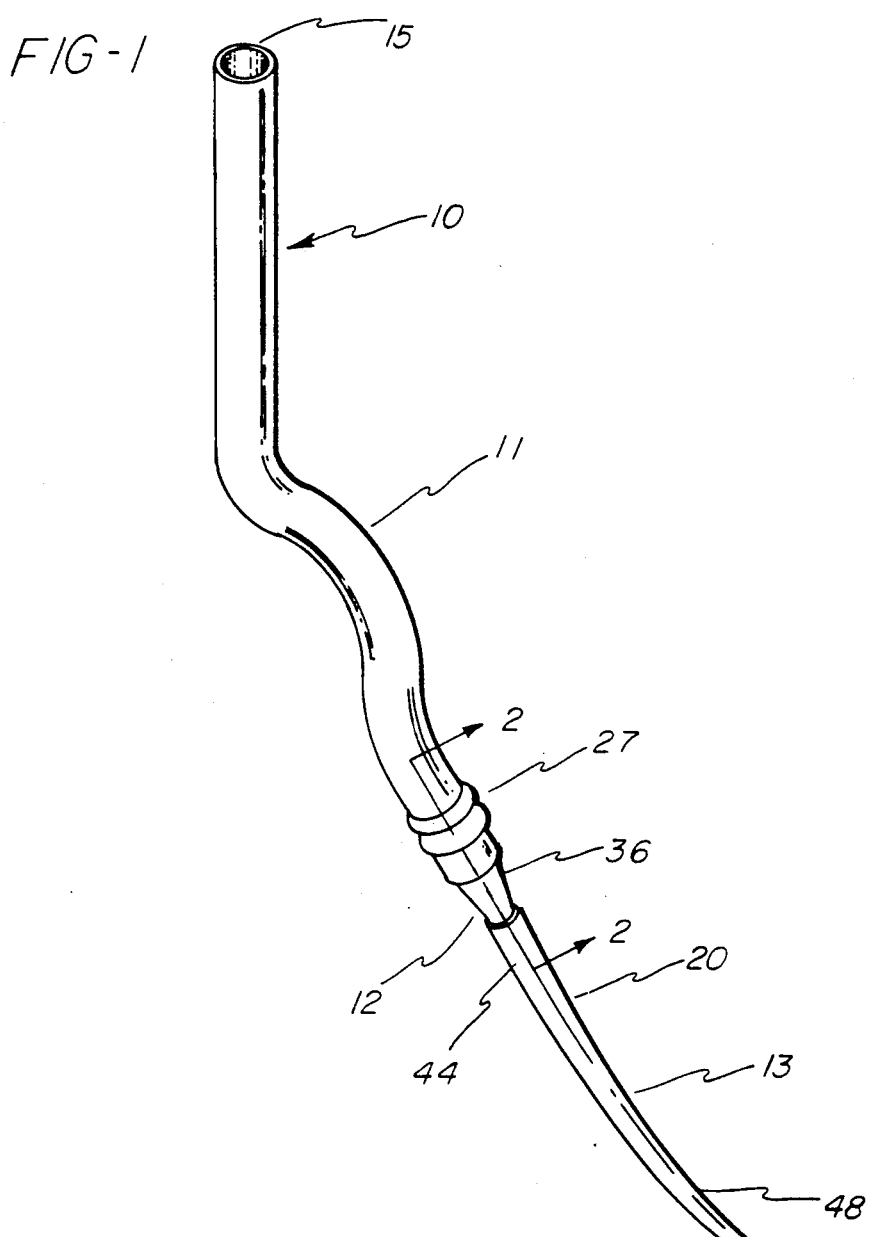
FIG. 1 is a perspective view of the stoma creator device in accordance with the present invention.

Having a reference to the drawings, attention is directed first to FIG. 1 which illustrates a stoma creator embodying this invention designated generally by the numeral 10. The basic components of this device 10 are a flexible tube 1, a barbed union 12 and a tapered dilator 13. The stoma creator 10 has a first opening 15 at its proximal end and a second opening 18 at its distal end with the diameter of the first opening 15 being greater than the diameter of the second opening 18. As can be seen, the first opening is at the one end of the flexible tube while the second opening 18 is at the tip of the tapered dilator 13. At its tip, the tapered dilator is approximately 5 French and gently tapers to the proximal end of the dilator 20 to approximately 14 French.

Preferably the flexible tube is fabricated from a silicone material with an interior diameter sufficiently large to accommodate a 22 French gastrostomy tube. The barbed union 12 preferably is fabricated from nylon. The tapered dilator which is semi-rigid, yet flexible, preferably is fabricated from polyethylene.

Figure 2:
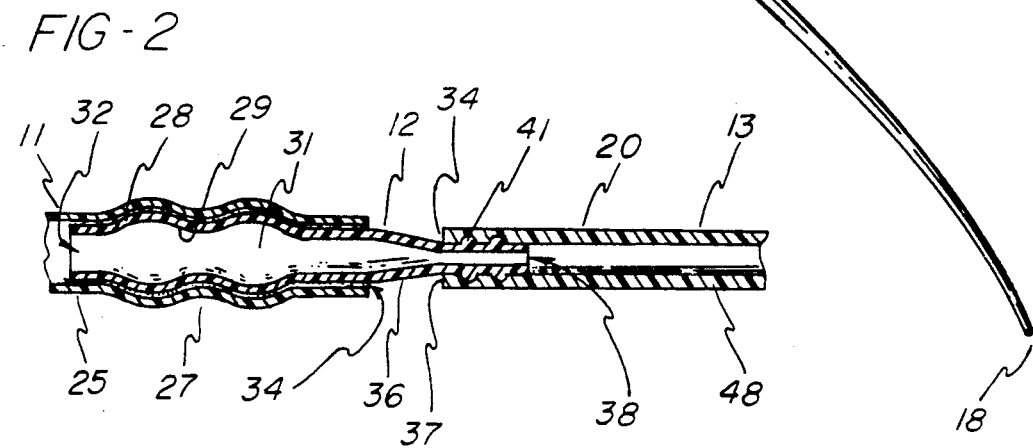
FIG. 2 is a vertical cross-sectional view on a greatly enlarge scale taken along line 2—2 of FIG. 1.

As can be seen in FIG. 2, tube side wall 25 of the distal tube end 27 is in frictional contact with union side wall 28. That portion of barbed union 12 features a first securing means 29 in the form of a gently undulating portion of the barbed union. The first securing means 29 is associated with the union first end portion 31, with union first end portion 31 having a first union aperture 32. The distal tube end 27 of flexible tube 11 is shown as being secured to the union first end portion 31 by an adhesive bond 34. That particular juncture can be subjected to corona discharge or plasma treated to enhance bond strength.

The barbed union 12 also has a tapered section 36 intermediate to the union first end portion 31 and a second end portion 37. Second end portion 37 has a second union aperture 38 in addition to barb 41. The second end portion 37 of tapered dilator of barbed union 12 is preferably subjected to an adhesive bond 34 between the dilator side wall 48 and the barb 41.

BEST MODE

FIGS. 3–12 disclose the method of utilizing the stoma creator of this invention to place a feeding tube utilizing a PEG procedure. As can be seen in FIG. 3, the body 50 is rolled into the supine position and an endoscope 52 is passed into mouth 55 and down esophagus 57 into stomach 60 which previously has been insufflated with air. At this time the room lights should be relatively dimmed and the endoscope 52 should be deflected to the interior surface of the stomach 60. An insertion site for a slotted needle should be chosen that is free of major vessels, viscera and scar tissue. This site is usually one third the distance from the left costal margin at the midclavicular line to the umbilicus. The intended insertion site should be depressed with finger 65. The endoscopist should clearly see the depression as the finger presses on abdominal wall 68.

As can be seen in FIG. 4, the insertion site having been prepared with a local anesthetic has hand 69 insert slotted needle 70, having at its tip a slot 71 into which fits a T-fastener 72 with a string 73 depending from T-fastener 72 upwardly along slotted needle 70, through the insertion site in the abdominal wall 68. A grommet 74 is located atop T-fastener stylet 75 which depends downwardly through the interior of slotted needle 70. As can be seen in FIG. 4, the grommet is disposed a short distance above the slotted needle such that the bottom portion of the T-fastener stylet is positioned just above slot 71.

As can be seen in FIG. 5, finger 65 depresses grommet 74 such that T-fastener stylet 75 passes downwardly through the slotted needle 70 so as to dislodge T-fastener 72 from slot 71. At the opposite end of the string 73 from the T-fastener 72 is a cotton pledget 76 atop which fits a nylon washer 77 and above which is positioned an aluminum crimp 78 which when crimped restricts the upward movement of both the nylon washer and cotton 77 pledget 76.

FIG. 6 shows the body 50 with endoscope 52 inside the stomach 60 following the placement of a plurality of T-fasteners preferably four in number. When the T-fastener is in its operative position, the T-fastener 72 is pulled upwardly towards abdominal wall 68 until the T-fastener is in contact with the interior of stomach wall 80. The stomach wall is then pulled slightly toward the abdominal wall 68 until the distance between the two is relatively minimal. At that point, the cotton pledget 76 is securely positioned above the opening since the slotted needle has now been withdrawn. The nylon washer 77 is placed on top of the pledget and the aluminum crimp 78 is secured in place. Once the T-fasteners are in place against the inner wall 82 of stomach wall 80, a stoma 84 is formed.

Following local anesthesia, an adequate skin incision is made to the anterior abdominal wall. Aiming slightly cephalad, a non-slotted needle 85 preferably a Seldinger needle, is inserted into the skin incision then through the abdominal wall into the stomach. When the endoscopist sees the Seldinger needle in the stomach, the inner stylet of such a needle is removed leaving the outer cannula or needle hub 87 in place. To assist in the procedure the polypectomy snare, which should have been previously passed through the endoscope's accessory channel, is loosely looped over the outer canula.

Figure 7:
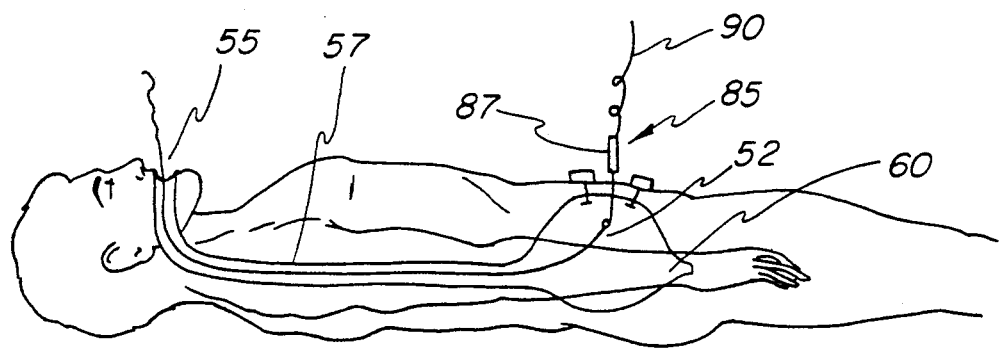
FIG. 7 is another schematic view showing the practice of the method of the current invention.

As can been seen in FIG. 7, a guidewire 90 is inserted through needle hub 87 of the non-slotted needle 85. When the guidewire is visualized in the stomach, the polypectomy snare is moved down the outer cannula so as to snare the guidewire. The endoscope and the polypectomy snare is then withdrawn from the stomach 60 as the guidewire 90 is freely fed into the cannula 87. The guidewire is then pulled through the esophagus and out of the mouth.

Figure 8:
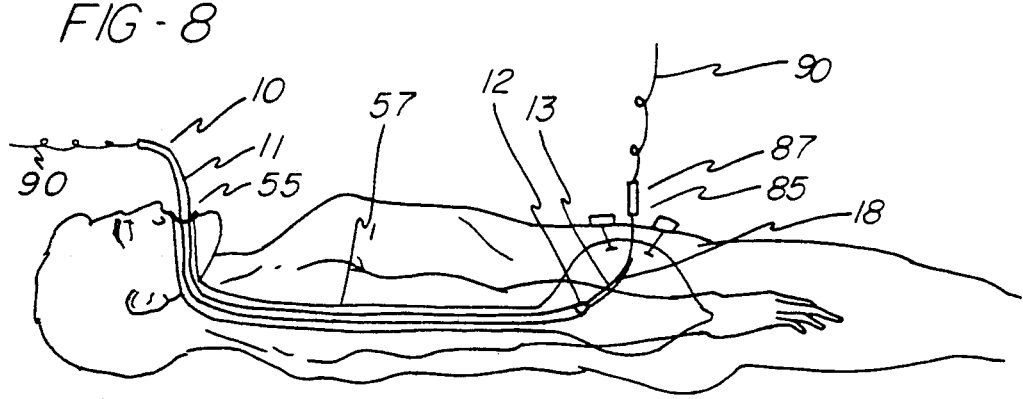
FIG. 8 is another schematic view showing the practice of the method of the current invention.

As can be seen in FIG. 8, the stoma creator 10 of this invention is threaded over guidewire 90, and in the preferred method is then passed into the oropharynx through the esophagus and into the stomach. Once in the stomach, the leading end of the tapered dilator 13 will meet the outer cannula 87 of the non-slotted needle 85 and will follow the tract of the cannula as it pushes the cannula back through the interior abdominal wall.

When the leading end of the stoma creator 10 emerges from the abdominal skin, the outer cannula 87 of the Seldinger needle 85 may be grasped, removed from the guidewire, and discarded. The tapered dilator 13 of the stoma creator, which is approximately 27" in length should then be grasped to assist in pulling the gently tapered portion of the dilator through the abdominal skin. After the tapered dilator as well as barbed union 12, is completely through the skin approximately another 2–3" of the preferably white silicone tube should be pulled through the stoma.

With the guidewire still in place, the tapered tube 11 should then be cut so as to sever the tapered dilator 13 and barbed union 12 from the rest of the stoma creator 10. In addition to having a portion of the flexible tube project through abdominal wall 68, the portion of the tube with first opening 15 also projects from mouth 55. Once the tube has been cut thereby forming a second tubular opening 95, the tapered dilator may then be removed from the guidewire and discarded.

Figure 9:
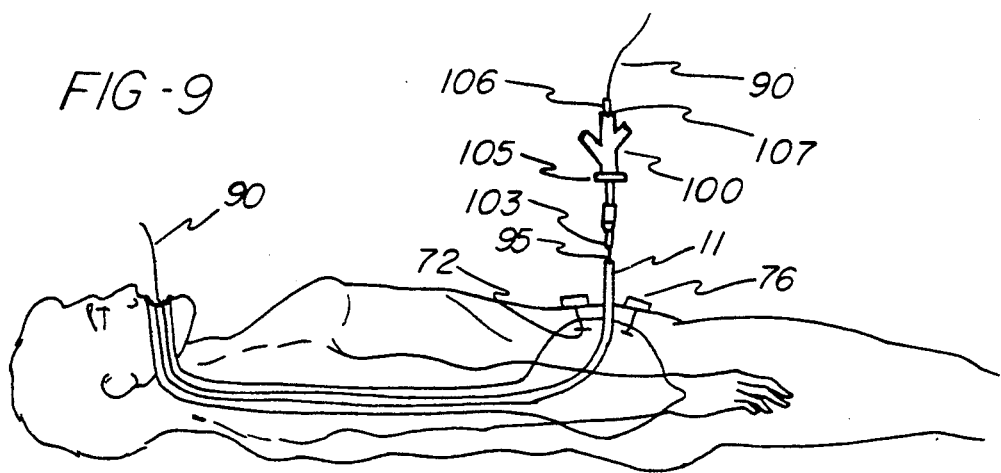
FIG. 9 is another schematic view showing the practice of the method of the current invention.
Figure 10:
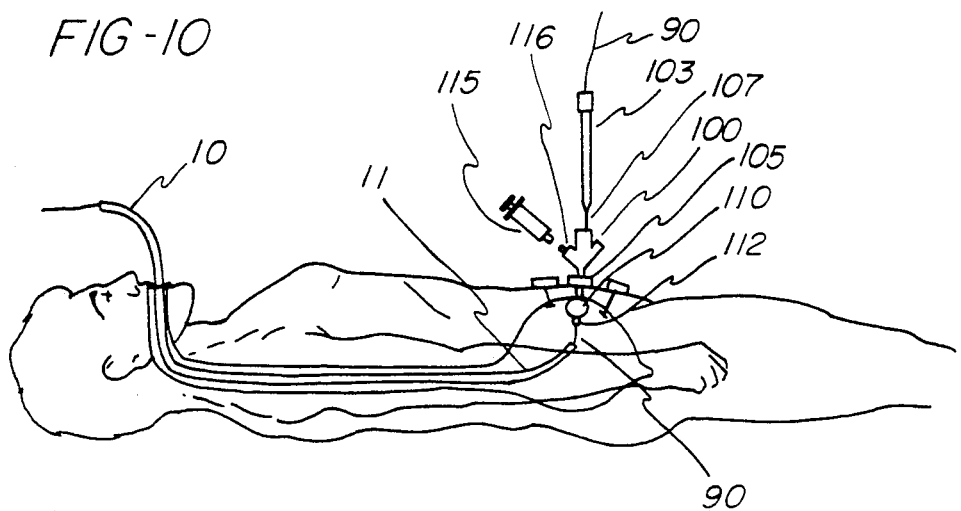
FIG. 10 is another schematic view showing the practice of the method of the current invention.

FIGS. 9 and 10 also disclose a gastrostomy tube 100, preferably one which is relatively flexible and having a gastrostomy tube stylet 103 inserted therethrough passed over guidewire 90 and moved toward the second tubular opening 95. The skin disk 105 associated with this flexible gastrostomy tube 100 is moved toward the Y-port connector of the gastrostomy tube. The tapered distal tip of the gastrostomy tube stylet 103 should protrude from the lower most portion of the gastrostomy tube 100.

A water soluble lubricant is preferably used to lubricate the outside surface of gastrostomy tube 100. The gastrostomy tube stylet 103 features a stylet hub 106 at its upper-most portion which should be moved adjacent feeding lumen 107 of the gastrostomy tube 100. Simultaneously then the gastrostomy tube and stylet should be pushed and the flexible tube 11 pulled so that the junction of the two tubes passes through the abdominal wall 68 and enters the stomach 60. When the junction is in the stomach, the balloon portion 100 of gastrostomy tube 100 is filled with approximately 20 cc of sterile saline or water. Once the balloon is filled to prevent the unintentional removal of the gastrostomy tube 100, the portion of the flexible tube 11 is pulled away from the tip 112 of the gastrostomy tube 100. The flexible tube portion 11 of stoma creator 10 may then pulled out of the stomach and removed from the guidewire. It can be seen in FIG. 9 that the balloon portion 100 of the gastrostomy tube is filled through the use of a syringe 115, with the liquid being injected through a valve component 116 of the gastrostomy tube 100.

Figure 11:
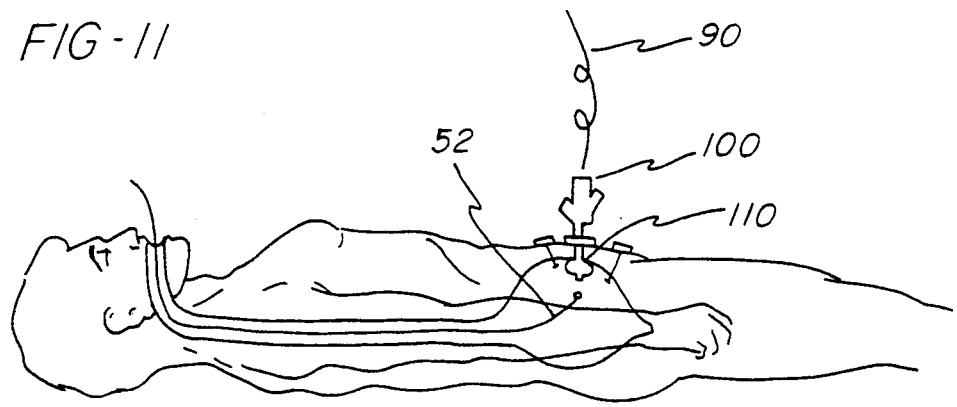
FIG. 11 is another schematic view showing the practice of the method of the current invention.

As can be seen in FIG. 11 the endoscope is passed into the stomach and under endoscopic guidance the proper positioning of the balloon 110 in relationship to the gastric mucosa is assured. The gastrostomy tube is secured in position by positioning of the skin disk 105 against the abdominal wall 68. The guidewire 90 may then be removed from the abdominal site.

Figure 12:
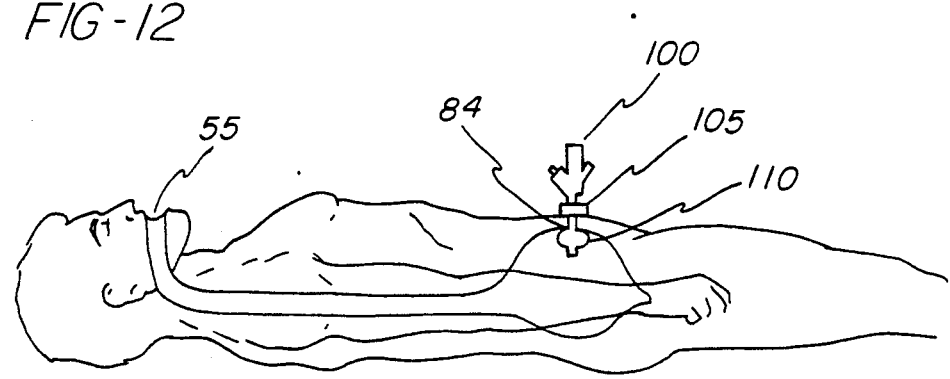
FIG. 12 is another schematic view showing the practice of the method of the current invention.

FIG. 12 discloses the feeding tube in position once the endoscope has been removed. Once scar tissue forms throughout the stoma, and a mature stoma tract is formed, the T-fasteners are no longer required and may be passed through the system by cutting suture 73.

INDUSTRIAL APPLICABILITY

The enteral feeding industry has sought ways to minimize the trauma and cost associated with the placement and removal of gastrostomy devices. This invention solves this long-felt need. A less traumatic placement and easier replacement of these devices is provided.

While the form of apparatus and method herein described constitute a preferred embodiment of this invention, it is to be understood that the invention is not limited to precise form of apparatus or method and that changes may be made therein without departing from the scope of the invention which is defined in the appended claims.

What is claimed is:

1. A stoma creator comprising:
   (a) a flexible tube fabricated from a silicone material and having an interior diameter sufficiently large to accommodate a gastrostomy tube;
   (b) a tapered dilator fabricated form polyethylene and having a sidewall which gently tapers from a larger size at a first end to a smaller size at a second end; and
   a connecting union fabricated from nylon, a first end portion of the connecting union comprising securing means in the form of an undulating sidewall inserted into an end of said flexible tube and secured thereto by an adhesive bond, a second end portion of the connecting union comprising securing means in the form of external ridges inserted into said first end of said tapered dilator and secured thereto by an adhesive bond.

2. A stoma creator according to claim 1 wherein the connecting union has a tapered section intermediate said first end portion and said second end portion.

3. A stoma creator according to claim 1 wherein said flexible tube has an interior diameter sufficiently large to accommodate a 22 French gastostomy tube and the sidewall of the tapered dilator gently tapers from approximately 14 French at said first end to about 5 French at said second end.

* * * * *